United States Patent [19]

Rhys-Davies

[11] 4,228,792
[45] Oct. 21, 1980

[54] EXSANGUINATING DEVICE FOR DISPLACING BLOOD FROM A LIMB BY COMPRESSION

[76] Inventor: Noel C. Rhys-Davies, Yeovil District Hospital, Higher Kingston, Yeovil, Somerset, England

[21] Appl. No.: 943,774

[22] Filed: Sep. 20, 1978

[30] Foreign Application Priority Data

Sep. 23, 1977 [GB] United Kingdom ............... 39781/77

[51] Int. Cl.³ .......................... A61H 9/00; A61H 15/00
[52] U.S. Cl. .................................... 128/24.3; 128/327
[58] Field of Search ............... 128/402, 297, 298, 299, 128/325, 327, 87 R, DIG. 20, 261, 157, 24.3

[56] References Cited

U.S. PATENT DOCUMENTS

| | | | |
|---|---|---|---|
| 2,068,173 | 1/1937 | Galves | 128/79 |
| 2,943,859 | 7/1960 | Koski et al. | 128/327 |
| 3,186,404 | 1/1965 | Gardner | 128/87 R |
| 3,282,414 | 11/1966 | Penska | 128/132 R |
| 3,678,936 | 7/1972 | McCormick | 128/402 |
| 4,153,054 | 5/1979 | Boone | 128/157 |

FOREIGN PATENT DOCUMENTS 237486 7/1925 United Kingdom ..................... 128/327

Primary Examiner—Robert W. Michell
Assistant Examiner—J. L. Kruter
Attorney, Agent, or Firm—Woodcock, Washburn, Kurtz, Mackiewicz & Norris

[57] ABSTRACT

An exsanguinating device for displacing blood from a limb by compression comprises a fluid-filled envelope in the form of a double-walled tube of elastomer with the inner and outer walls of the same unstressed dimensions. The device can roll onto the limb with the inner and outer walls exchanging positions. The inner surface of the envelope is preferably lubricated to prevent sticking where the inner wall folds at the ends. When a liquid fill is used this can serve as the lubricant.

6 Claims, 3 Drawing Figures

EXSANGUINATING DEVICE FOR DISPLACING BLOOD FROM A LIMB BY COMPRESSION

The present invention relates to a device for exsanguinating a limb.

Such a device is used when it is desired to exsanguinate a limb so that surgery can be carried out in a "bloodless field". One known method of achieving this is for the patient's arm or leg to be elevated above his heart, for example for 5 minutes, whereafter an inflatable cuff at the uppermost part of the limb is raised to a pressure greater than the blood pressure of the patient. This method suffers from the disadvantage that only venous blood is drained from the arm before the tourniquet is applied. The arterial and capillary blood remains.

Another known method which overcomes this disadvantage is the use of a rubber elastic bandage approximately 2" wide and 5 to 6' in length. This bandage is wound around the arm from the fingers, overlapping the turns of the bandage up the arm, the bandage being stretched before each turn is applied. Whilst this bandage produces a satisfactory degree of exsanguination, the use of the bandage involves an undesirable delay after a patient has been anaesthetised and before a surgeon can commence an operation. This method also suffers from the disadvantage that the pressure which is applied varies widely according to the force which is applied and the degree of overlap of the turns of the bandage. Further, the bandage cannot be used on limbs having fractures or open wounds, owing to the lateral forces applied to the limb during application of the bandage.

According to the invention there is provided a device for exsanguinating a limb comprising a double walled cylindrical tubular body of elastomeric material of which the inner and outer walls have substantially the same unstressed dimensions and are interconnected at their ends to form a continuous envelope which can be fitted with a fluid under pressure so that the fluid pressure distends the outer wall and partially collapses the inner wall, wherein the outer surface of the envelope is free of protrusions such that it can roll along a limb inserted in one end of the tubular body with the inner and outer walls constantly exchanging positions and will progressively compress the limb by virtue of the pressure of the contained fluid.

Preferably the device is made of rubber. It may have a self-sealing valve for filling of the envelope with air or other gas under pressure so that filling can be effected at the place of use and any leakage during use can be made good. The valve should be designed to create no significant concentration of pressure so that the pressure on the limb is as uniform as possible.

Alternatively a liquid may be used to fill the envelope in which case the filling inlet is permanently sealed. The liquid is preferably an oil or grease which will serve as a lubricant for the inner surface of the envelope. Where the envelope is filled with gas a coating of lubricant such as oil, grease or powdered graphite is desirable on the inner surface of the envelope. This lubrication is provided to prevent sticking of the inner surface against itself in the end regions where the transition is made from the distened outer wall to the collapsed inner wall, the latter tending to fold upon itself.

In the following description a preferred exsanguination device is described as being applied to an arm. However, it should be understood that the device could equally well be used on a leg.

Figure 1:
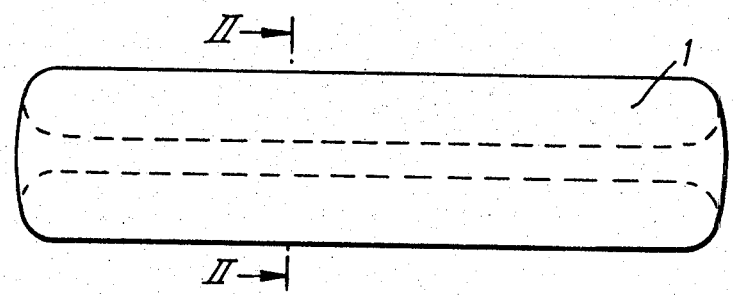
FIG. 1 shows a side view of an exsanguination device according to the invention when inflated.

As shown in the drawings, the exsanguination device comprises a body in the form of a double-walled cylinder 1 of rubber or other elastomeric material, having enclosed ends and an outer wall 2 and an inner wall 3. The resultant body comprises an inner cylinder and an outer cylinder which equate with one another dimensionally and physically, being formed of a memory cured elastomer which will exert uniform pressure without surface tension. The outer and inner walls are interconnected at their ends to form a continuous envelope with a smooth surface on the outside and the inside of the cylinder. The device also comprises a one-way self sealing valve 4, which may be of conventional design, which allows the device to be inflated by means of a pump or other source of compressed gas.

Figure 2:
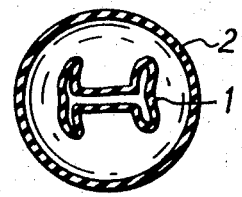
FIG. 2 shows a section through the device of FIG. 1 on line II—II.
Figure 3:
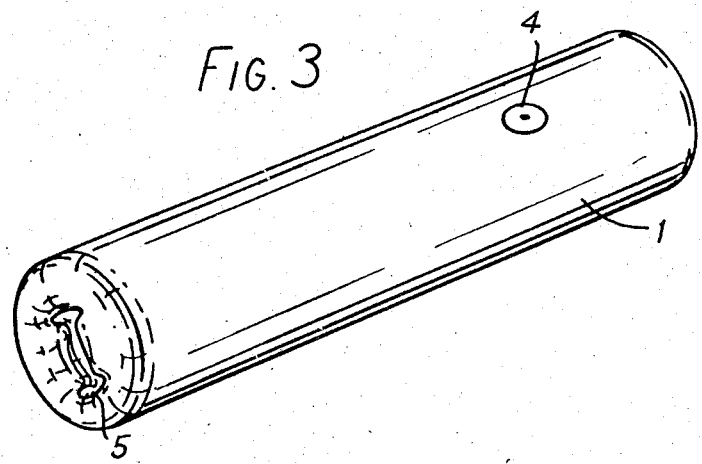
FIG. 3 shows a perspective view of the device of FIGS. 1 and 2.

Upon inflation the outer and inner walls, which are initially, in the unstressed condition, of the same dimensions, are pushed apart, the outer wall being distended to a cylinder of larger diameter while the inner wall is at least partially-collapsed, as seen in the cross-section of FIG. 2.

Alternatively the envelope is filled with a liquid in which case the valve 4 is replaced by an inlet which is sealed off after introduction of the liquid.

The inner surface of the envelope is coated with a surface lubricant such as an oil or grease to prevent sticking of the inner surface to itself particularly at the ends where it becomes folded. In the case of a liquid filling the liquid itself may serve as the lubricant.

It will be noted that the axial length of the cylinder is several times greater than the diameter of the inflated cylinder and is of a length sufficient to extend over a substantial part of a human limb.

The device is applied as follows; An operator inserts his hand into the end 5 of the cylinder 1 and rolls the cylinder onto his arm. The operator then grasps the hand of the anaesthetised patient and allows the cylinder to roll off his arm and onto the arm of the patient. The cylinder can then be rolled up the arm of the patient as far as a deflated torniquet cuff already in place on the patient's arm and indeed moves somewhat in the manner of the endless track of a tracked vehicle. With the cylinder inflated to the correct pressure, blood in the limb will be forced out of the limb and beyond the torniquet which can then be inflated. After the cuff has been inflated to the desired pressure, the cylinder can be allowed to roll off the arm of the patient. This rolling occurs because a human arm tapers to the wrist, so that the cylinder always has a tendency to run down the arm. The device can be allowed to remain, more or less permanently, in the inflated condition.

The length of the inflated cylinder is preferably 18", this being the length from the wrist joint to the axilla of the arms of normal individuals. It has been found that substantially similar dimensions are required of a device for use on a leg. Similarly, there is no necessity for different dimensions or pressure for application to a child's limb.

Satisfactory results have been obtained with a double walled cylinder made of rubber of 2 mm thickness having a Young's modulus of 360 psi, which, when inflated to a pressure of 50 mm Hg forms a cylinder of length 18" and produces a pressure around a limb of 75 mm Hg. In order to provide a device capable of producing a higher pressure on the limb, rubber of 2 mm thickness and having a Young's modulus of 540 psi or 3 mm thickness and having a Young's modulus of 360 psi may be used. Such a device is capable of producing a pressure around a human limb of in excess of 90 mm Hg.

The exsanguination device described has numerous advantages. Thus it can be kept to hand permanently inflated or filled with liquid and ready for use and can thus be applied very quickly. If desired, traction can be applied to the limb during application, thus allowing the use of the device on fractured limbs. The fact that an even pressure and only minimum surface friction will be applied around the circumference of a limb allows the use of the device even on limbs having deep wounds or over open surgery. As it rolls along a limb, a moving front of pressure is applied, thus tending to force blood from the limb. Further, the device requires no external monitoring equipment and it is non-technical in application. Finally, the entire exsanguination operation using the device can be carried out in seconds.

I claim:

1. A device for exsanguinating a limb comprising a double-walled elongated cylindrical tubular body of elastomeric material of which the inner and outer walls have substantially the same unstressed dimensions and are interconnected solely at their ends to form a continuous envelope which is filled with a fluid under pressure so that the fluid pressure distends the outer wall and partially collapses and expands the inner wall inwardly to substantially fill the inner space, wherein the outer surface of the envelope is free of protrusions such that as a limb is inserted in either end of the tubular body the inner and outer walls constantly exchange positions and the inner wall will progressively compress the limb by virtue of the pressure of the contained fluid.

2. A device as claimed in claim 1 having a self-sealing valve for filling of the envelope with gas under pressure.

3. A device as claimed in claim 1 or 2 in which the inner surface of the envelope is coated with a lubricant to prevent sticking of the envelope at its ends.

4. A device as claimed in claim 1 in which the envelope is filled with a liquid and sealed, the liquid being such as to serve as a lubricant for the inner surface of the envelope.

5. A method of exsanguinating a limb wherein said limb is inserted into a device in accordance with claim 1 to effect progressive compression thereof.

6. A method as claimed in claim 5 in which a tourniquet cuff is inflated to exert pressure on said limb after the limb has been inserted into the device and the device is thereafter removed.

* * * * *